United States Patent
Storey et al.

(10) Patent No.: US 10,506,667 B2
(45) Date of Patent: Dec. 10, 2019

(54) EVAPORATOR

(71) Applicant: OGLESBY & BUTLER RESEARCH & DEVELOPMENT LIMITED, Carlow (IE)

(72) Inventors: John Joseph Storey, County Laois (IE); Jacqueline Oglesby, Carlow (IE); Rachel Samantha Purcell, Carlow (IE); Alfred Peter Oglesby, County Louth (IE)

(73) Assignee: OGLESBY & BUTLER RESEARCH & DEVELOPMENT LIMITED, Carlow (IE)

( * ) Notice: Subject to any disclaimer, the term of this patent is extended or adjusted under 35 U.S.C. 154(b) by 717 days.

(21) Appl. No.: 15/028,978

(22) PCT Filed: Oct. 20, 2014

(86) PCT No.: PCT/IE2014/000018
§ 371 (c)(1),
(2) Date: Apr. 13, 2016

(87) PCT Pub. No.: WO2015/056252
PCT Pub. Date: Apr. 23, 2015

(65) Prior Publication Data
US 2016/0270155 A1    Sep. 15, 2016

(30) Foreign Application Priority Data

Oct. 18, 2013  (IE) .................................. S2013/0320

(51) Int. Cl.
*H05B 3/00*    (2006.01)
*A01M 1/20*    (2006.01)
(Continued)

(52) U.S. Cl.
CPC ......... *H05B 3/0014* (2013.01); *A01M 1/2077* (2013.01); *A61L 9/03* (2013.01);
(Continued)

(58) Field of Classification Search
CPC ................ A01M 1/2077; A61M 15/08; A61M 2205/3368; A61M 2205/8206; A61M 11/042; A61L 9/03; H05B 3/0014
(Continued)

(56) References Cited

U.S. PATENT DOCUMENTS 2,616,024 A    10/1952    Laibow
2,690,500 A  *  9/1954    Winberg ............. A01M 1/2077
                                                     126/390.1
(Continued)

FOREIGN PATENT DOCUMENTS

BE    867 793 A1    10/1978
JP    1057464    *    2/1998    .......... A01M 1/2077
(Continued)

OTHER PUBLICATIONS

International Search Report of PCT/IE2014/000018, dated Apr. 15, 2015. [PCT/ISA/210].
(Continued)

*Primary Examiner* — Dana Ross
*Assistant Examiner* — Kuangyue Chen
(74) *Attorney, Agent, or Firm* — Sughrue Mion, PLLC

(57) ABSTRACT

An evaporator (1) comprises a housing (2) having a top wall (7) in which a receiving recess (14) is formed for receiving a container (15) for a liquid to be evaporated. A heat transfer element (30) having a first heat transfer abutment face (35) located in the receiving recess (14) transfers heat from an electrically powered heating element (25) to the container (15) through a second heat transfer abutment face (36) of a base (16) of the container (15). The heating element is planar
(Continued)

and is located between the heat transfer element (30) and a locating element (40), which retains the heating element (25) tightly between the heat transfer element (30) and the locating element (40). A retaining magnet (48) located in the locating element (40) extends into a bore (52) in the heat transfer element (30) and co-operates with a complementary element (49) of magnetic material located in the base (16) of the container (15) for releasably retaining the container (15) in the receiving recess (14).

20 Claims, 8 Drawing Sheets

(51) Int. Cl.
*A61L 9/03* (2006.01)
*A61M 15/08* (2006.01)
*A61M 11/04* (2006.01)

(52) U.S. Cl.
CPC ............ *A61M 11/042* (2014.02); *A61M 15/08* (2013.01); *A61M 2205/3368* (2013.01); *A61M 2205/8206* (2013.01)

(58) Field of Classification Search
USPC ........................................................ 392/403
See application file for complete search history.

(56) References Cited

U.S. PATENT DOCUMENTS

| | | | |
|---|---|---|---|
| 5,485,671 A * | 1/1996 | Larson | F28D 15/0241 165/104.19 |
| 6,861,628 B2 * | 3/2005 | Owens | A47J 36/2483 219/387 |
| 2003/0064002 A1 | 4/2003 | Jaworski et al. | |
| 2005/0016985 A1 * | 1/2005 | Haas | A61L 9/03 219/438 |
| 2005/0184045 A1 | 8/2005 | Shimizu et al. | |
| 2007/0194144 A1 * | 8/2007 | Davis | A61L 9/03 239/34 |
| 2008/0149624 A1 * | 6/2008 | Tamura | H02J 7/00 219/685 |
| 2008/0149665 A1 * | 6/2008 | Hafer | A01M 1/2077 222/3 |
| 2011/0103776 A1 | 5/2011 | Jorgensen | |
| 2012/0080537 A1 | 4/2012 | Walter | |
| 2013/0283896 A1 * | 10/2013 | Matsuzawa | F02M 25/0854 73/114.39 |

FOREIGN PATENT DOCUMENTS

| | | | | |
|---|---|---|---|---|
| JP | 10-57464 A | 3/1998 | | |
| WO | 2005/112510 A1 | 11/2005 | | |
| WO | WO-2005112510 A1 * | 11/2005 | ......... | A01M 1/2077 |
| WO | 2008/046908 A1 | 4/2008 | | |
| WO | 2012/140637 A1 | 10/2012 | | |

OTHER PUBLICATIONS

Written Opinion of PCT/IE2014/000018, dated Apr. 15, 2015. [PCT/ISA/237].

* cited by examiner

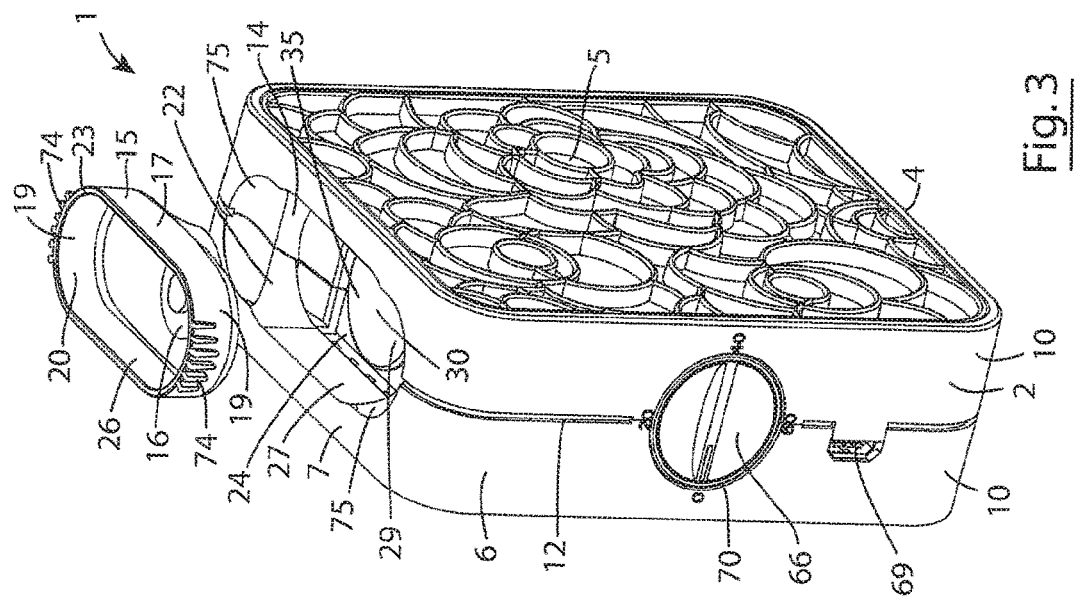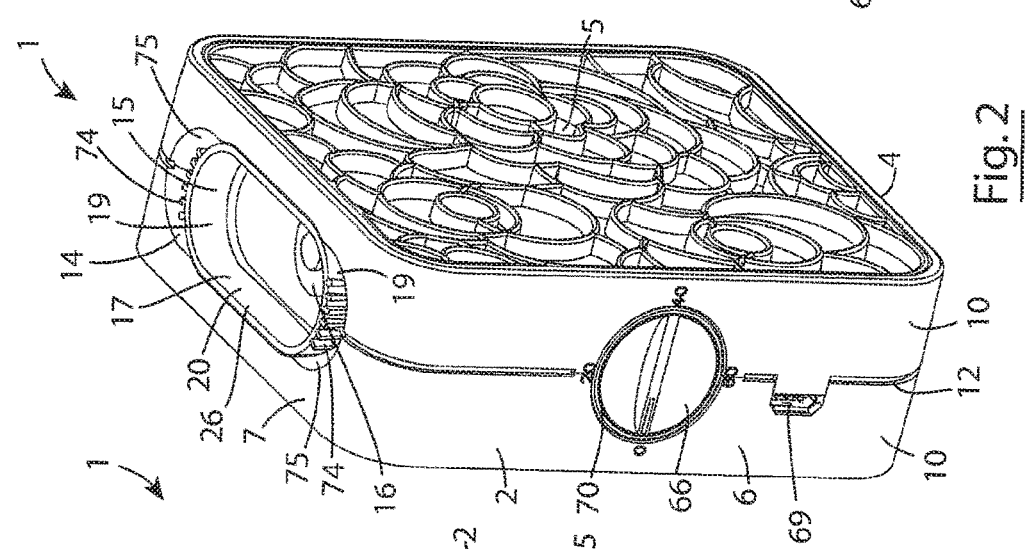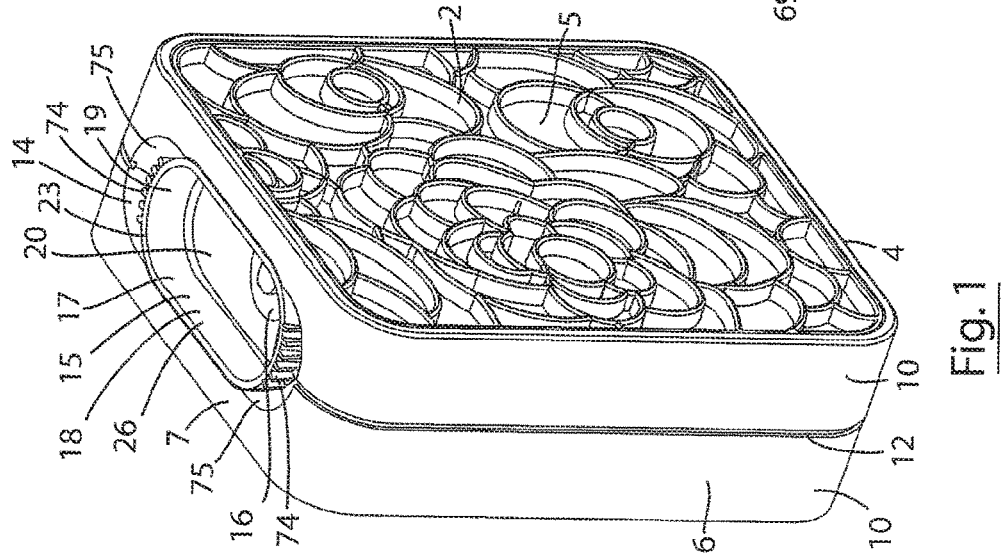

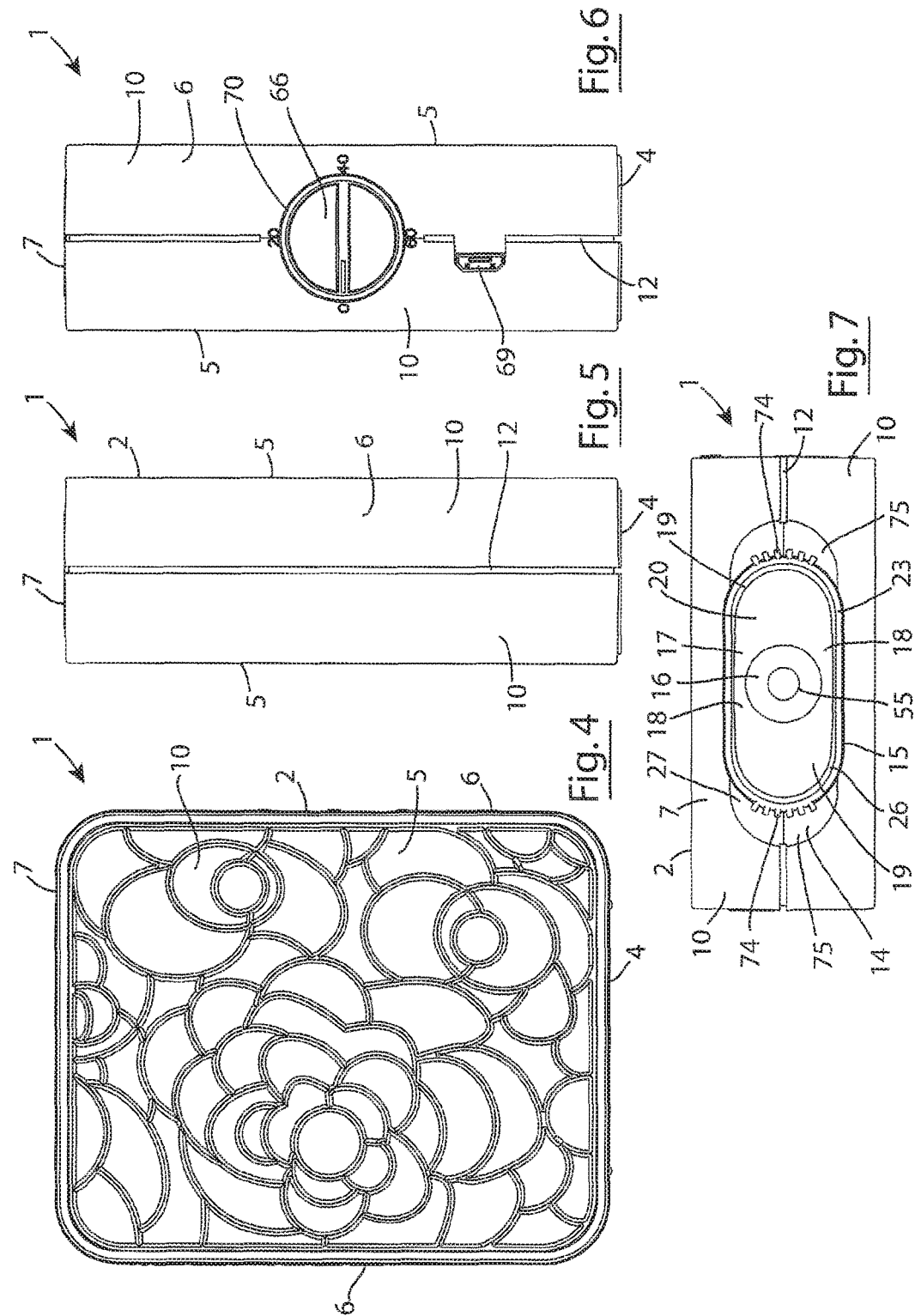

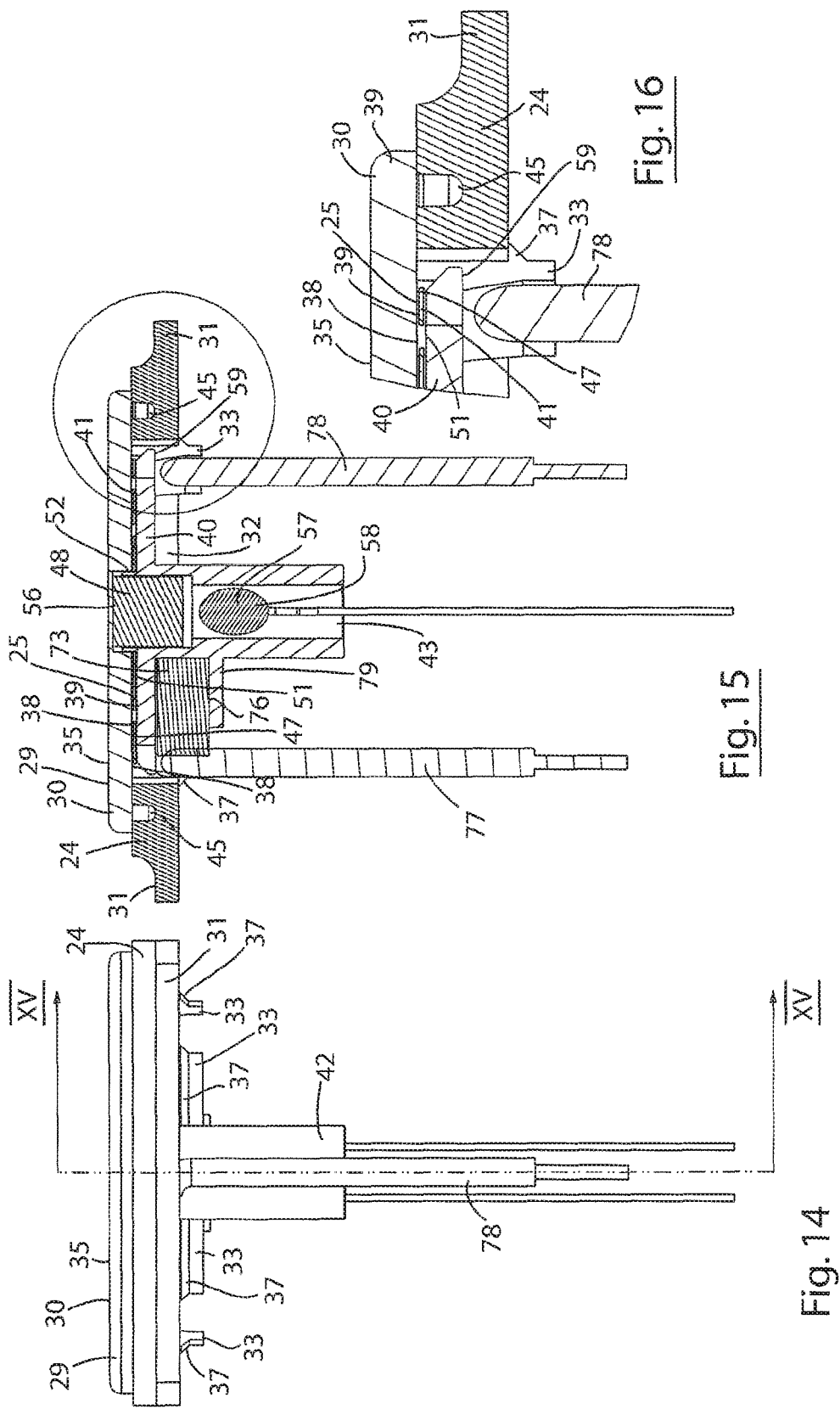

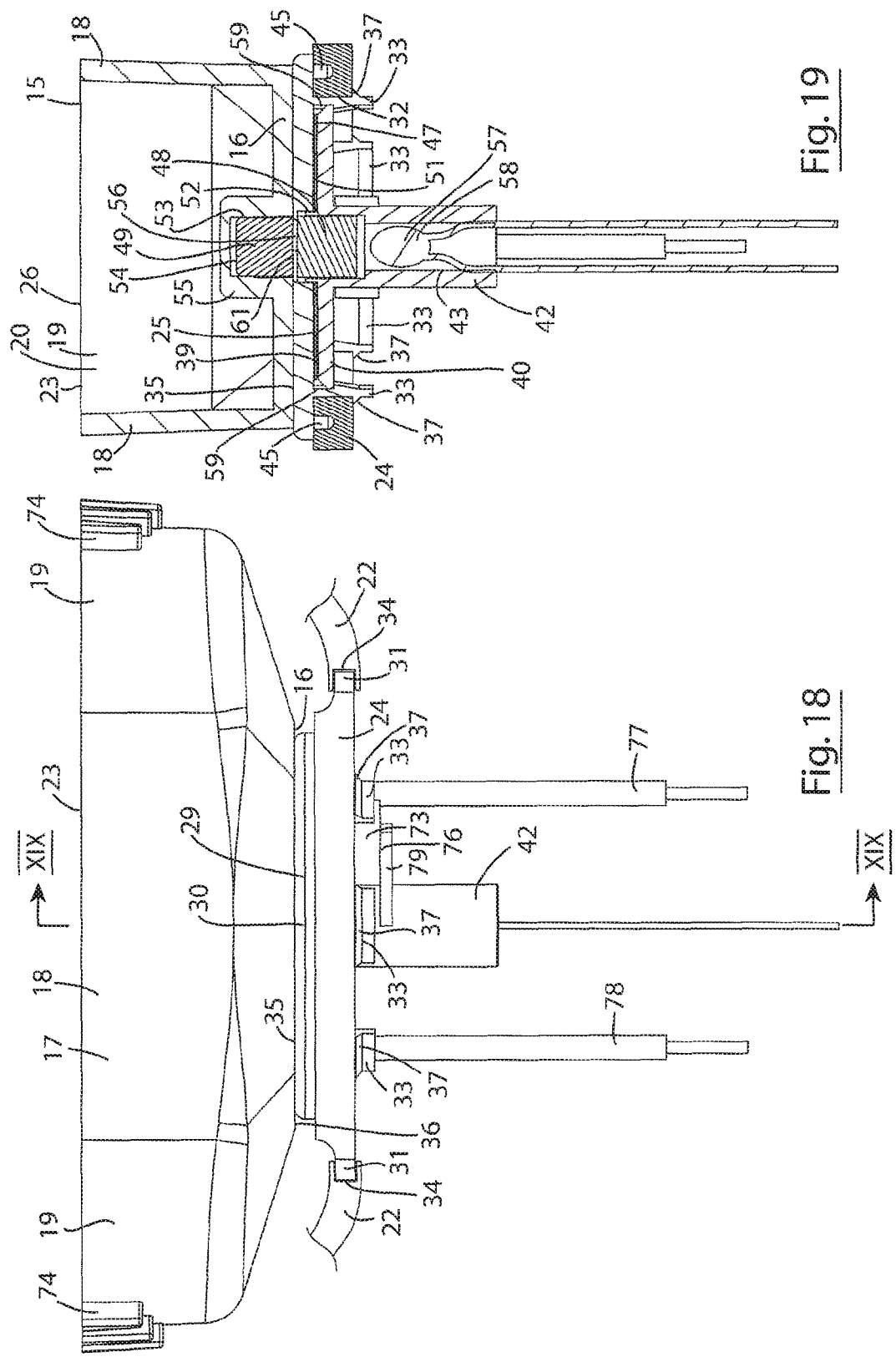

EVAPORATOR

CROSS REFERENCE TO RELATED APPLICATIONS

This application is a National Stage of International Application No. PCT/IE2014/000018 filed Oct. 20, 2014, claiming priority based on Irish Patent Application No. S2013/0320, filed Oct. 18, 2013, the contents of all of which are incorporated herein by reference in their entirety.

The present invention relates to an evaporator, and in particular, though not limited to an evaporator for evaporating an essential oil, for example, an aromatherapy oil.

Evaporators for evaporating oils, and in particular essential oils, are known. Such evaporators typically comprise a housing of a ceramics material, at the top of which an open mouth container for the essential oil is formed. The open mouth of the container faces upwardly for accommodating the evaporate of the essential oil from the container. A burner chamber is located in the housing beneath the essential oil container for accommodating a burner in order to heat the essential oil container. The burner chamber in general is of size to receive a burner of the type commonly referred to as a "night light". Such night lights comprise a relatively shallow hollow cylinder filled with solidified wax. A wick is embedded in the solidified wax and extends from the wax. A flame burning on the wick heats the essential oil container above the burner chamber to in turn evaporate the essential oil. In general, such evaporators are provided as one-piece units, and in general are of a ceramics material. The essential oil container should be cleaned and washed after each use, and because such evaporators are provided as one-piece units, cleaning and washing the essential oil container proves relatively difficult.

Other types of evaporators are gas powered evaporators and electrically powered evaporators. In general, similar problems arise with such gas and electrically powered evaporators, in that cleaning and washing the essential oil container after use proves quite difficult.

A gas powered essential oil evaporator is disclosed in PCT published Application Specification No. WO 2012/140637 of Oglesby which comprises a gas powered heater. The gas powered heater converts fuel gas to heat by a catalytic action. Heat from the gas powered heater is transferred to a container for the essential oil. While the essential oil container is removable from this evaporator, removal and engagement of the essential oil container with the evaporator is relatively cumbersome and difficult.

There is therefore a need for an evaporator which addresses at least some of the problems of prior art evaporators.

The present invention is directed towards providing such an evaporator.

According to the invention, there is provided an evaporator comprising a housing, a container for a liquid to be evaporated, a receiving means in the housing for releasably receiving the container supported therein, a heating means, a heat transfer means for transferring heat from the heating means to the container, the heat transfer means being configured to co-operate with the container for the transfer of heat from the heat transfer means to the container, and a retaining means for releasably retaining the container in the receiving means with the container in heat conducting engagement with the heat transfer means.

Preferably, the heat transfer means is located in the receiving means.

In one aspect of the invention the heat transfer means defines a first heat transfer abutment face.

Preferably, the container comprises a heat receiving portion having a second heat transfer abutment face configured to abut the first heat transfer abutment face of the heat transfer means with heat conducting engagement. Advantageously, the first and second heat transfer abutment faces are of complementary shape one to the other. Ideally, the first and second heat transfer abutment faces are planar.

In one aspect of the invention the first and second heat transfer abutment faces are of substantially circular shape.

Preferably, the heat transfer means comprises a heat conductive material. Advantageously, the heat transfer means comprises a metal material. Ideally, the heat transfer means comprises aluminium.

In one aspect of the invention the container comprises a base, the base of the container defining the heat receiving portion thereof. Preferably, the base of the container defines the second heat transfer abutment surface.

In another aspect of the invention the retaining means is located in one of the receiving means and the container. Preferably, the retaining means comprises a magnet. Advantageously, the retaining means comprises a permanent magnet. Ideally, the retaining means comprises a heat conducting material.

In another aspect of the invention a complementary element is provided for co-operating with the retaining means for releasably retaining the container in the receiving means, the complementary element being located in the one of the receiving means and the container in which the retaining means is not located.

In one embodiment of the invention the complementary element is located in the container. Preferably, the complementary element is located in the base of the container. Advantageously, a boss extends from the base of the container into the container and the complementary element is located in a bore extending through the base into the boss from the second heat transfer abutment face.

Preferably, the complementary element terminates flush with the second heat transfer abutment face. Advantageously, the complementary element is configured to engage the heat transfer means for transferring heat from the retaining means into the container.

In one aspect of the invention the complementary element comprises a magnetic material. Preferably, the complementary element is of heat conducting material. Advantageously, the complementary element comprises a metal material.

In another aspect of the invention the retaining means is located in the heat transfer means. Preferably, the retaining means is located in a bore in the heat transfer means.

In one aspect of the invention the heating means is in heat conducting engagement with the heat transfer means.

Preferably, the heat transfer means defines a third heat transfer abutment face configured to abut the heating means. Advantageously, the third heat transfer abutment face of the heat transfer means is located opposite the first heat transfer abutment face thereof. Preferably, the third heat transfer abutment face of the heat transfer means extends substantially parallel to the first heat transfer abutment face thereof. Advantageously, the third heat transfer abutment face of the heat transfer means is of substantially circular shape.

In another aspect of the invention the heating means defines a fourth heat transfer abutment face configured to abut the third heat transfer abutment face of the heat transfer means.

Preferably, the third and fourth heat transfer abutment faces of the heat transfer means and the heating means, respectively, are substantially planar.

In another aspect of the invention an engagement means extending from the heat transfer means is engageable with an opening in the receiving means for securing the heat transfer means in the receiving means. Preferably, the engagement means comprises a plurality of engagement members extending from the heat transfer means spaced apart circumferentially around the heat transfer means.

In one aspect of the invention the heating means is located within the engagement means.

In another aspect of the invention a locating means is provided for locating and maintaining the heating means in heat conducting engagement with the heat transfer means. Preferably, the locating means comprises a substantially planar locating element.

Preferably, the locating means is located within the engagement means of the heat transfer means and is retained in abutting engagement with the heating means by the engagement means. Advantageously, the locating means is retained relative to the heat transfer means by the engagement means, so that the heating means is retained tightly sandwiched between the locating means and the heat transfer means.

In one aspect of the invention the heating means defines a fifth heat transfer abutment face opposite the fourth heat transfer abutment face thereof engageable with a sixth heat transfer abutment face defined by the locating means with heat conducting engagement.

Preferably, the fifth and sixth heat transfer abutment faces are planar.

Advantageously, the fourth and fifth heat transfer abutment faces extend parallel to each other.

In another aspect of the invention the heating means is configured to be electrically powered. Preferably, the heating means comprises a planar heating element. Advantageously, the heating element of the heating means comprises an elongated heating element configured in a serpentine shape. Ideally, the heating means comprises an electrically resistive element.

In one aspect of the invention the third heat transfer abutment face of the heat transfer means is coated with an electrically insulated coating. Preferably, the heat transfer means is coated with an anodised coating.

In another aspect of the invention the locating means comprises a heat conductive material. Preferably, the locating means comprises a metal material. Advantageously, the locating means comprises aluminium.

In another aspect of the invention the sixth heat transfer abutment face of the locating means is coated with an electrically insulating coating. Preferably, the locating means comprises a substantially circular shaped disc element.

In a further aspect of the invention a tubular element extends from the locating means in a direction away from the heating means and defines a bore extending therethrough communicating with a bore extending through the locating means.

In another aspect of the invention the retaining means is located in the bore of the tubular element and extends through the sixth heat transfer abutment face defined by the locating means.

Advantageously, the locating means is configured to transfer heat from the heating means to the retaining means.

In a further aspect of the invention the retaining means extends through an opening defined by the heating means and into the bore in the heat transfer means for transferring heat from the locating means to the heat transfer means.

In a still further aspect of the invention the heat transfer means, the locating means and the retaining means form a thermal mass for stabilising the temperature of the heat transfer means.

In one aspect of the invention a temperature sensing means is provided for monitoring the temperature adjacent the container. Preferably, the temperature sensing means is configured to monitor the temperature of the heat transfer means. Advantageously, the temperature sensing means is located in the bore extending through the tubular member of the locating means.

In another aspect of the invention the tubular element is located substantially centrally relative to the locating means.

In another aspect of the invention a control means is provided for controlling the heating means in response to temperature sensed by the temperature sensing means for maintaining the temperature of the heat transfer means at a predefined normal operating temperature. Preferably, the predefined normal operating temperature is selectable.

In another aspect of the invention the heating means is battery powered.

Preferably, a battery for powering the heating means is provided. Advantageously, the battery comprises a rechargeable battery. Ideally, the control means is configured for controlling charging of the battery.

In another aspect of the invention a timing means is provided for timing a heating cycle time period for heating the container. Preferably, the timing means is configured so that the duration of the heating cycle time period is selectable.

In one aspect of the invention the housing defines a hollow interior region.

In another aspect of the invention the receiving means comprises a receiving recess formed in the housing, and a partition element of the housing separates the receiving recess from the hollow interior region of the housing.

Preferably, the engagement means of the heat transfer means is configured for engaging an opening in the partition element.

In one aspect of the invention the heat transfer means comprises a planar element.

Preferably, the receiving means substantially defines the container.

In one aspect of the invention the container comprises a peripheral wall extending upwardly from and around the base of the container and defining with the base of the container a hollow interior region for the liquid which is to be evaporated. Preferably, the peripheral wall of the container terminates in an upper peripheral edge defining an open mouth to the hollow interior region of the container. Advantageously, the peripheral wall of the container tapers inwardly downwardly towards the base of the container.

In another aspect of the invention the housing comprises a base wall, a pair of spaced apart side walls extending upwardly from the base wall, a pair of spaced apart end walls extending upwardly from the base wall and joining the side walls at respective opposite ends thereof, and a top wall extending between the side and end walls.

Preferably, the base wall, the side and end walls and the top wall define the hollow interior region of the housing.

Advantageously, the receiving means is located in the top wall of the housing.

Preferably, the battery, the control means, the temperature sensing means and the timer are located in the hollow interior region of the housing.

Advantageously, the heating element is located in the hollow interior region of the housing.

The advantages of the invention are many. The evaporator according to the invention is a relatively efficient evaporator, and efficiently evaporates essential oils or other liquids contained in the container. The configuration of the retaining means permits the container to be readily easily removed and replaced in the receiving means. Additionally, the heat transfer means efficiently transfers heat from the heating means into the container, which results in efficient evaporation of the essential oil or other liquids with minimum energy requirement. In particular, the location of the complementary element in the boss extending into the container further enhances the heat transfer efficiency with which heat is transferred from the heating means to the container, and in turn to the essential oil or other liquid to be evaporated.

A further advantage of the invention is achieved by the provision of the control means and the temperature sensing means which allow the heat transfer means and in turn the container to be maintained at a substantially constant predefined normal operating temperature during evaporation of the essential oil or other liquid, thereby avoiding any danger of boiling of the essential oil or other liquid.

The invention will be more clearly understood from the following description of a preferred embodiment thereof, which is given by way of example only, with reference to the accompanying drawings, in which:

FIG. 1 is a perspective view of an evaporator according to the invention,

FIG. 2 is another perspective view of the evaporator of FIG. 1,

FIG. 3 is an exploded perspective view of the evaporator of FIG. 1,

FIG. 4 is a front elevational view of the evaporator of FIG. 1,

FIG. 5 is an end elevational view of the evaporator of FIG. 1,

Figure 8:
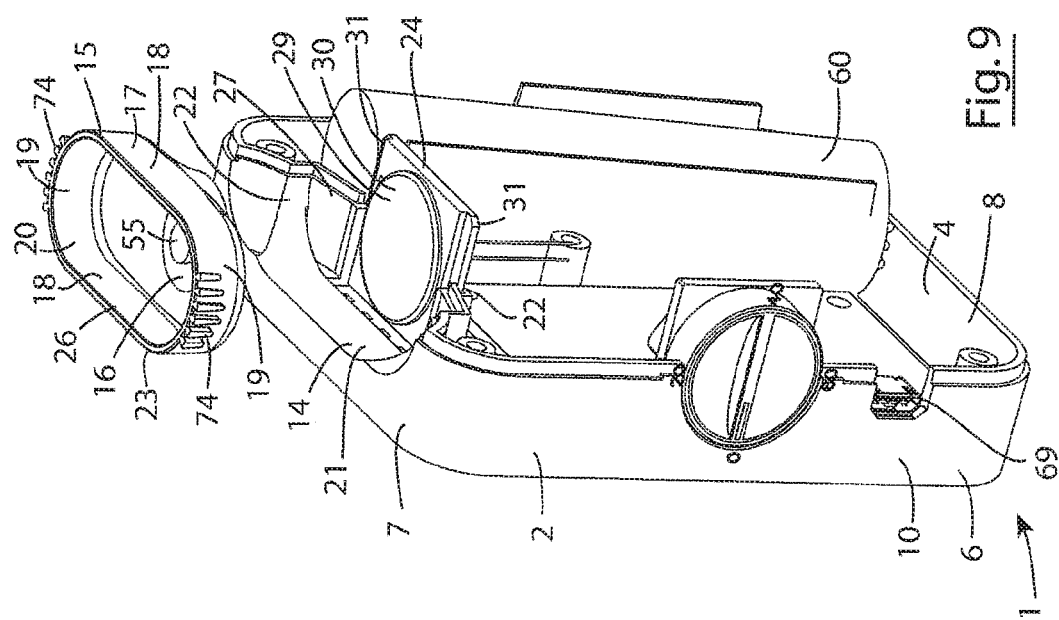
Figure 9:
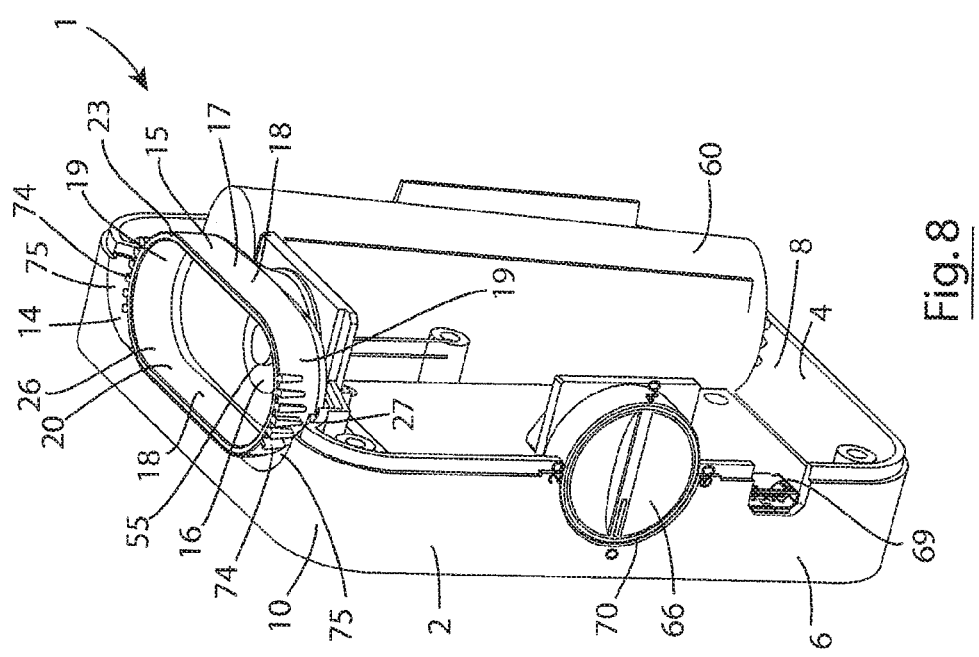
Figure 10:
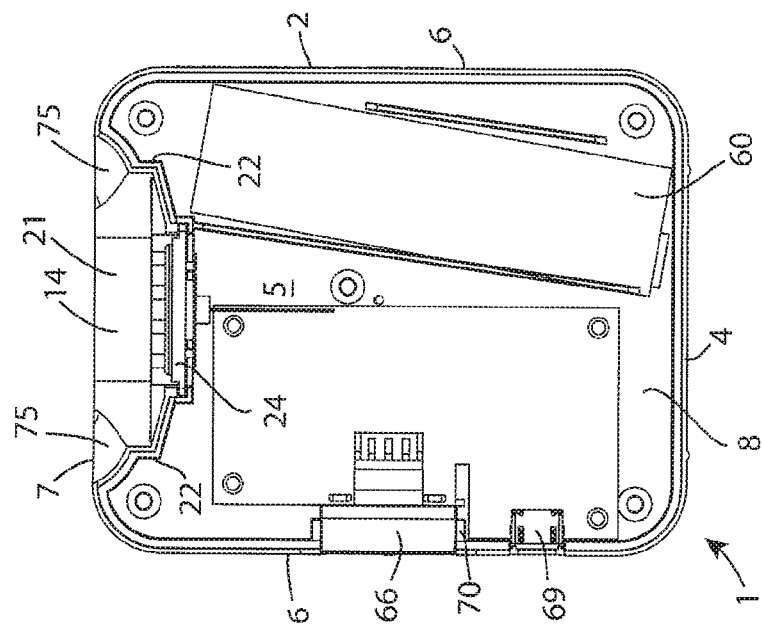
Figure 11:
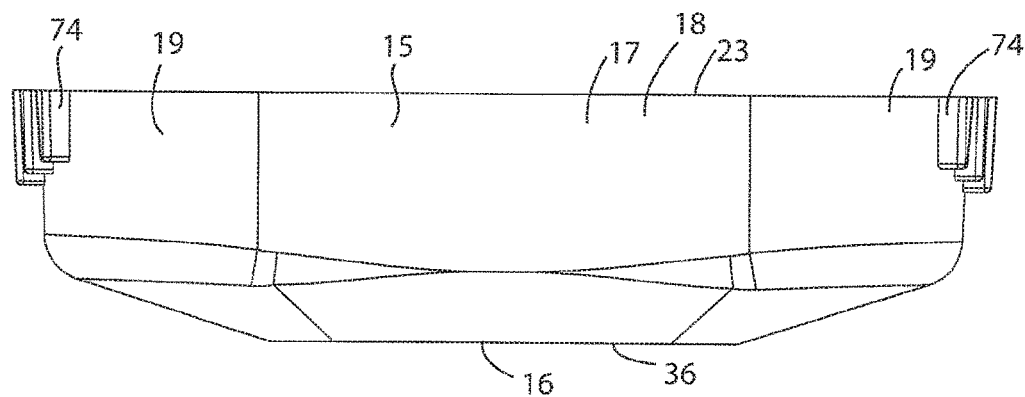
Figure 13:
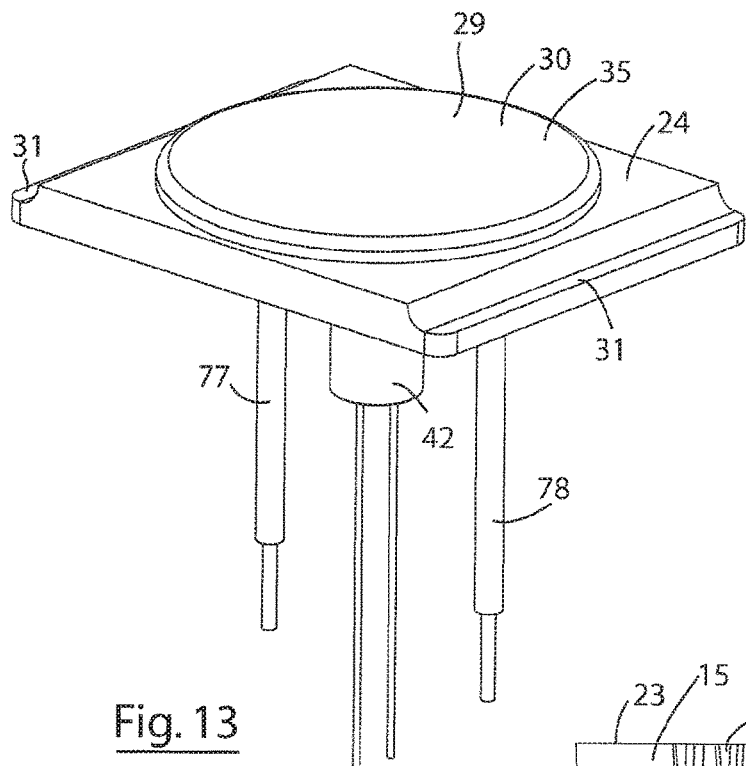
Figure 12:
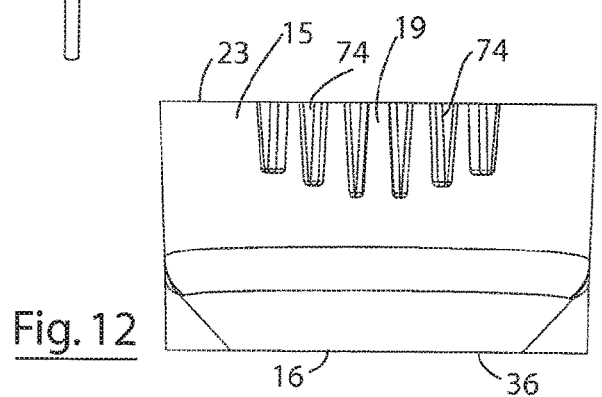
Figure 20:
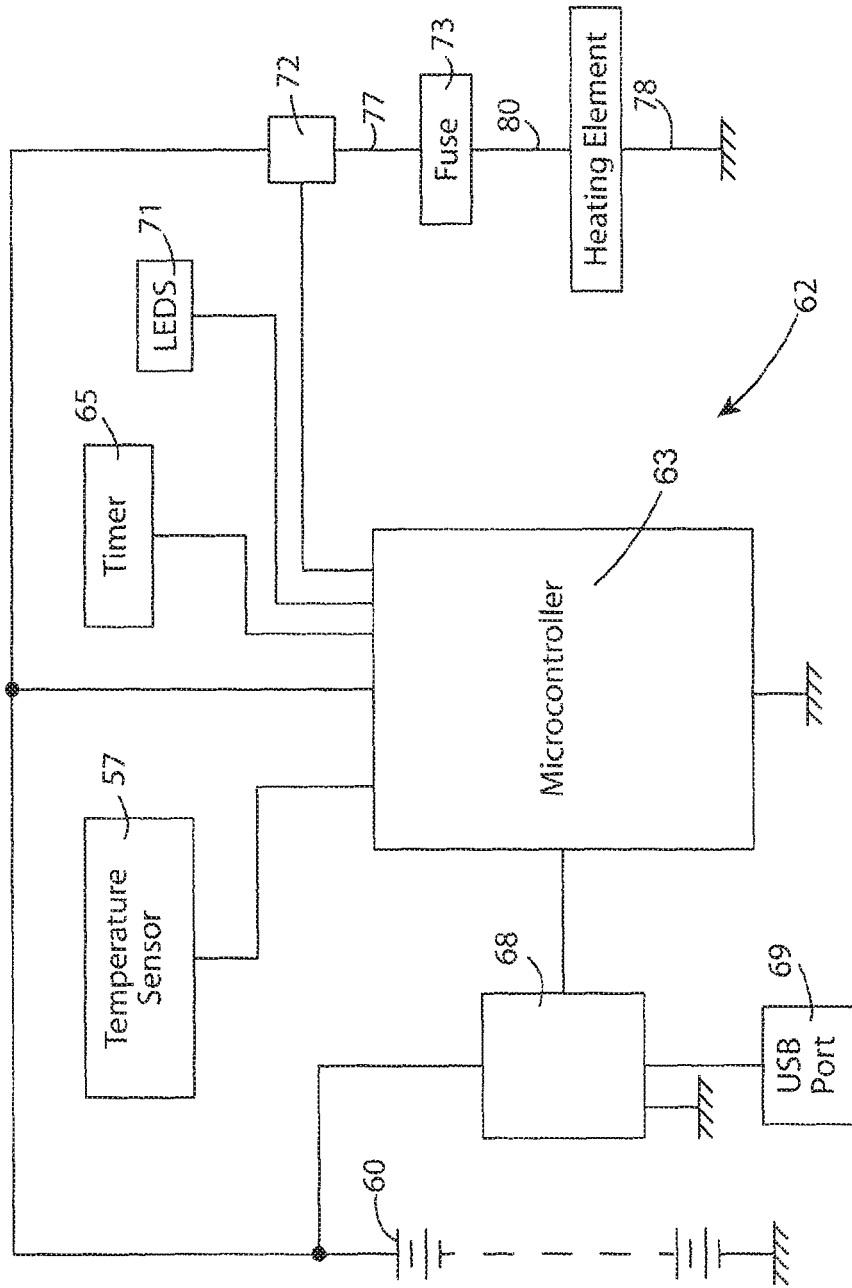

FIG. 6 is an end elevational view of the evaporator of FIG. 1 from the opposite end to that of FIG. 5, FIG. 7 is top plan view of the evaporator of FIG. 1, FIG. 8 is a partly cut-away perspective view of the evaporator of FIG. 1, FIG. 9 is a partly cut-away exploded perspective view of the evaporator of FIG. 1, FIG. 10 is a partly cut-away front elevational view of the evaporator of FIG. 1, FIG. 11 is a front elevational view of a portion of the evaporator of FIG. 1, FIG. 12 is an end elevational view of the portion of FIG. 11 of the evaporator of FIG. 1, FIG. 13 is a perspective view of a portion of the evaporator of FIG. 1, FIG. 14 is a side elevational view of the portion of FIG. 13 of the evaporator of FIG. 1, FIG. 15 is a cross-sectional end elevational view of the portion of FIG. 13 of the evaporator of FIG. 1 on the line XV-XV of FIG. 14, FIG. 16 is an enlarged view of a detail of the portion of FIG. 13 of the evaporator of FIG. 1, FIG. 17 is an exploded perspective view of the portion of FIG. 13 of the evaporator of FIG. 1, FIG. 18 is a front elevational view of the portion of FIG. 13 of the evaporator of FIG. 1 with the portion of FIG. 11 mounted thereon, FIG. 19 is a cross-sectional end elevational view of the portions of FIGS. 13 and 11 of the evaporator of FIG. 1 on the line XIX-XIX of FIG. 18, and FIG. 20 is a block representation of a circuit diagram of the evaporator of FIG. 1.

Referring to the drawings, there is illustrated an evaporator according to the invention indicated generally by the reference numeral 1 for evaporating a liquid, for example, an essential oil of the type used in aromatherapy. The evaporator 1 comprises a housing 2 of plastics material, which comprises a base wall 4, a pair of spaced apart side walls 5 extending upwardly from the base wall 4, a pair of spaced apart end walls 6 extending upwardly from the base wall 4 and joining the side walls 5 at respective opposite ends thereof. A top wall 7 joins the side and end walls 5 and 6. The base wall 4, the side walls 5, the end walls 6 and the top wall 7 define a hollow interior region 8 of the housing 2. The housing 2 is formed by a pair of half shells 10 of injection moulded plastics material which are joined along a seam 12 which extends along the base wall 4, the end walls 6 and the top wall 7. One of the half shells 10 forms one of the side walls 5 and half of each of the base wall 4, the end walls 6 and the top wall 7, while the other one of the half shells 10 forms the other side wall 5, and the other half of each of the base wall 4, the end walls 6 and top wall 7.

A receiving means comprising a receiving recess 14 is formed in the top wall 7 for receiving a container 15 for the liquid which is to be evaporated. The container 15 is of a composite plastics material with good heat conducting properties, and which is temperature resistant well above the temperatures to which it will be subjected. The composite plastics material of the container 15 is also chemically resistant to the liquids, such as essential oils, which are to be evaporated therefrom. The container 15 comprises a base 16 and a peripheral wall 17 extending around and upwardly from the base 16. The peripheral wall 17 is formed by a pair of side walls 18 extending upwardly from the base 16 and a pair of end walls 19 of arcuate shape which extend upwardly from the base 16 and join the side walls 18. A lower portion of the side and end walls 18 and 19 of the container 15 incline downwardly inwardly towards the base 16. The base 16 and the side and end walls 18 and 19 define a hollow interior region 20 for the liquid to be evaporated. The side walls 18 and the end walls 19 of the container 16 terminate in an upper peripheral edge 23 which defines an upwardly facing open mouth 26 to the hollow interior region 20 of the container 15 for accommodating evaporate of the liquid from the hollow interior region 20 therethrough.

Returning now to the receiving recess 14, the receiving recess 14 substantially defines the container 15 and is formed by a partition element 27 which separates the receiving recess 14 from the hollow interior region 8 of the housing 2. The partition 27 comprises a pair of opposite spaced apart side walls 21 which are joined by spaced apart arcuate end walls 22. The side and end walls 21 and 22 are of similar material to that of the housing 2, and are integrally formed with the housing 2. The side walls 21 and the end walls 22 extend downwardly from the top wall 7 of the housing 2, and lower portions of the respective side and end walls 21 and 22 incline inwardly downwardly to a base 24, so that the base 24, the side walls 21 and the end walls 22 together form the receiving recess 14. The base 24 of the receiving recess 14 is of substantially square shape and is formed separately of the housing 2 of a plastics material which is heat resistant to temperatures well in excess of the temperatures to which it is subjected. Opposite end edges of the base 24 are stepped to form respective tongues 31, which engage corresponding grooves 34 formed in the lower ends of the end walls 22.

A heating means comprising an electrically powered heating element 25, which will be described in detail below, is provided for heating the container 15 to evaporate the liquid therein. The heating element 25 comprises a planar heating element of an electrically resistant material terminating in a pair of connector tabs 28 for connecting the heating element 25 to an electrical power supply which is described below.

A heat transfer means, namely, a heat transfer element 30 comprising a planar heat transfer disc element 29 is located in an opening 32 extending through the base 24 of the receiving recess 14 for transferring heat from the heating elements 25 to the container 15. An engagement means comprising a plurality of circumferentially spaced apart arcuate engaging members 33 extend downwardly from the heat transfer disc element 29 for engaging and securing the heat transfer element 30 in the opening 32 in the base 24 of the receiving recess 14. Lugs 37 extending radially outwardly from the engagement members 33 engage the base 24 of the receiving recess 14 with the base 24 engaged between the heat transfer disc element 29 and the lugs 37. The heat transfer element 30 is of heat conductive material, which in this embodiment of the invention is a metal material, namely, aluminium. The heat transfer disc element 29 is of circular shape and defines a first major heat transfer abutment face 35 for abutting a second major heat transfer abutment face 36 defined by the base 16 of the container 15 with heat conducting engagement for conducting heat from the heating element 25 to the container 15. Both the first and second heat transfer abutment faces 35 and 36 are of circular shape and are planar so that the first and second heat transfer abutment faces 35 and 36 abut each other with heat conducting engagement.

The heat transfer disc element 29 defines a third major heat transfer abutment face 38 from which the engagement members 33 extend, and which is opposite to and parallel with the first heat transfer abutment face 35. The third heat transfer abutment face 38 is planar and engages the heating element 25 with heat conducting engagement for transferring heat from the heating element 25 through the heat transfer disc element 29 to the container 15 by heat conduction.

A locating means comprising a circular planar locating disc element 40 of heat conductive material, namely, aluminium is located within the engagement members 33 of the heat transfer element 30 for locating and maintaining the heating element 25 sandwiched tightly between the heat transfer disc element 29 and the locating element 40. Grooves 59 extending inwardly into the respective engagement members 33 adjacent the heat transfer disc element 29 engage the locating element 40, and are dimensioned so that the locating element 40 is retained tightly against the heating element 25 with the heating element 25 tightly sandwiched between the heat transfer disc element 29 and the locating element 40. A tubular element 42 also of heat conductive material, namely, aluminium extends centrally from the locating element 40 and defines a bore 43 of circular transverse cross-section extending therethrough and through the locating element 40 for a purpose to be described below.

Returning now to the heating element 25, in this embodiment of the invention the heating element 25 comprises an elongated heating element comprising an elongated electrically resistive conductor 41 configured into a serpentine shape and extending between the connector tabs 28. The conductor 41 is of rectangular cross-section, so that when formed into the serpentine shape, the heating element 25 is planar and defines a planar fourth major heat transfer abutment face 39 for abutting the third heat transfer abutment face 38 of the heat transfer disc element 29 with heat conducting engagement for transferring heat from the heating element 25 to the heat transfer disc element 29. Additionally, the heat transfer disc element 29 defines a planar fifth major heat transfer abutment face 47 which is opposite to and parallel with the fourth heat transfer abutment face 39. The fifth heat transfer abutment face 47 of the heating element 25 is engageable with a planar sixth major heat transfer abutment face 51 defined by the locating element 40 for transferring heat from the heating element 25 to the locating element 40. Accordingly, when the heating element 25 is tightly located between the heat transfer disc element 29 and the locating element 40, heat is transferred from the heating element 25 into the heat transfer disc element 29 through the third and fourth heat transfer abutment faces 38 and 39 and from the heating element 25 to the locating element 40 through the fifth and sixth heat transfer abutment faces 47 and 51.

The third heat transfer abutment face 38 of the heat transfer disc element 29 is coated with an electrically insulating coating, which in this embodiment of the invention comprises an anodised coating for electrically insulating the heat transfer disc element 29 from the conductor 41 of the heating element 25. The sixth heat transfer abutment face 51 of the locating element 40 is also coated with an electrically insulated coating, which in this embodiment of the invention also comprises an anodised coating for electrically insulating the locating element 40 from the conductor 41 of the heating element 25.

A circular groove 45 is formed in the base 24 of the receiving recess 14 extending around and spaced apart from the opening 32 to minimise heat transfer into the base 24 from the heating element 25 and the heat transfer element 30, and in turn minimising heat transfer into the housing 2.

A retaining means for retaining the container 15 in the receiving recess 14 and in heat conducting engagement with the heat transfer disc element 29 comprises a retaining element, namely, a retaining magnet 48, which in this embodiment of the invention comprises a permanent magnet. The retaining magnet 48 is located in the bore 40 of the tubular element 42, which extends from the locating element 40, and extends from the bore 43 through the sixth heat transfer abutment face 51 of the locating element 40. The retaining magnet 48 extends from the bore 43 through an opening 50 defined by the heating element 25, and engages a central bore 52 which extends into the heat transfer disc element 29 from the third heat transfer abutment face 38, and which is aligned with the bore 43 of the locating element 40. The central bore 52 terminates within the heat transfer disc element 29, and a distal end 56 of the retaining magnet 48 terminates at the end of the central bore 52, thereby maximising heat transfer from the retaining magnet 48 into the heat transfer disc element 29.

A complementary element 49 of a magnetic material, namely, mild steel is located in the base 16 of the container 15 and is aligned with the retaining magnet 48 when the container 15 is correctly located in the receiving recess 14, so that the retaining magnet 48 co-operates with the complementary element 49 for retaining the container 15 in the receiving recess 14. The complementary element 49 is located in a bore 53 extending into a boss 55 in the base 16 of the container 15 from the second heat transfer abutment face 36 thereof. The complementary element 49 terminates in a distal end 61 which lies flush with the second heat transfer abutment face 36 defined by the base 16 of the container 15 for abutting the heat transfer disc element 29. The boss 55 extends from the base 16 into the hollow interior region 20 of the container 15, and the bore 53 terminates in the boss 55, so that the bore 53 is sealably isolated from the hollow interior region 20 of the container 15. An upper end 54 of the complementary element 49 terminates with the bore 53 in the boss 55. In this embodiment of the invention the complementary element 49 is of cylindrical shape and engages the bore 53 with a press fit, which provides good heat transfer engagement between the complementary element 49 and the boss 55 as well as the container 15.

The retaining magnet 48 is also of cylindrical shape of diameter similar to that of the complementary element 49 and forms a press fit in the bore 43 of the locating element 40 and the tubular element 42, so that the retaining magnet 48 is secured in the bore 43 with good heat transfer engagement between the locating element 40 and the tubular element 42 on the one hand and the retaining magnet 48 on the other hand. Since the retaining magnet 48 terminates in the heat transfer disc element 29, heat is transferred between the locating element 40 and the heat transfer element 30, so that the combination of the heat transfer element 30, the locating element 40 and the tubular element 42 act as an integral thermal mass, thereby stabilising the temperature of the heat transfer element 30, and minimising temperature fluctuations in the heat transfer element 30. Additionally, since the complementary element 49 terminates flush with the second heat transfer abutment face 36 of the base 16 of the container 15, when the container 15 is retained in the recess 14 by the co-operating action of the retaining magnet 48, as well as heat being transferred from the heat transfer disc element 29 into the base 16 of the container 15, heat is also transferred from the heat transfer disc element 29 through the complementary element 49.

The interior of the receiving recess 14 is shaped, and the exterior of the container 15 is shaped so that the interior of the receiving recess 14 substantially defines the exterior of the container 15, and therefore, the container 15 is essentially self-locating in the retaining recess 14 as the retaining magnet 48 acts on the complementary element 49 to draw the container 15 into the receiving recess 14 with the base 16 of the container 15 tightly abutting the heat transfer disc element 29. Additionally, when the container 15 is located in the receiving recess 14 with the second heat transfer abutment face 36 of the container 15 in heat conducting abutting engagement with the first heat transfer abutment face 35 of the heat transfer element 30, and is retained therein by the co-operating action between the retaining magnet 48 and the complementary element 49, the upper peripheral edge 23 of the side and end walls 21 and 22 of the container 15 is substantially flush with the top wall 7 of the housing 2.

A plurality of projecting elements 74 project outwardly from the respective end walls 19 of the container 15 to facilitate gripping of the container 15 for removal and insertion of the container 15 into the receiving recess 14. Finger and thumb accommodating recesses 75 are formed into the top wall 7 of the housing 2 and the end walls 22 of the receiving recess 14 to accommodate a finger and thumb of a user during removal and replacement of the container 15 in the recess 14.

A temperature sensing means comprising a thermistor 57 terminating in a bulb 58 is located in the bore 43 extending through the tubular element 42 of the locating element 40 for monitoring the temperature of the tubular element 42 and the locating element 40, and in turn the temperature of the heat transfer disc element 29. The bulb 58 of the thermistor 57 is cemented by a suitable heat conductive bonding cement in the bore 43 of the tubular element 42. Wires 67 from the thermistor 57 are accommodated downwardly through the bore 43 in the tubular element 42.

Turning now to the powering and control of the operation of the evaporator 1, and referring in particular to FIG. 20, a rechargeable battery 60 located in the hollow interior region 8 of the housing 2 powers the heating element 25 through a control means, namely, a control circuit 62. The control circuit 62 comprises a signal processor, namely, a microcontroller 63 which reads signals from the thermistor 57 and in turn determines the temperature of the heat transfer element 30. The heating element 25 is powered from the battery 60 through a relay 72 and a fuse 73. The fuse 73 is described below. The microcontroller 63 operates the relay 72 to control the power supply to the heating element 25 in response to the temperature of the heat transfer element 30 for maintaining the temperature of the heat transfer element 30 at a predefined normal operating temperature. The predefined normal operating temperature in some embodiments of the invention may be selectable. However, in this embodiment of the invention, the predefined normal operating temperature at which the heat transfer element 30 is maintained is pre-set during manufacture of the evaporator 1, and is suitable for evaporating the essential oil at a predefined rate suitable for aromatherapy. Typically, the predefined normal operating temperature at which the heat transfer element 30 is maintained lies in the range of 40° C. to 100° C., and more typically, lies in the range of 55° C. to 70° C., and even more typically lies in the range of 55° C. to 60° C., although depending on the oil or liquid to be evaporated and the desired evaporation rate, the evaporator may be supplied with the predefined normal operating temperature pre-set at a higher or lower temperature than a temperature in the range of 55° C. to 100° C.

The fuse 73 is a temperature sensitive fuse and is located abutting the locating element 40 in a recess 76 formed between the locating element 40 and a lug 79 extending from the tubular element 42. A wire 77 from the relay 72 connects one terminal of the fuse 73 to the relay 72. The other terminal of the fuse 73 is connected to one of the connector tabs 28 of the heating element 25 by a wire 80. A wire 78 connects the other one of the connector tabs 28 of the heating element 25 to ground. The fuse 73 is configured to transition from a closed circuit state to an open circuit state on the temperature of the locating element 40 exceeding a predefined safe operating temperature, which is well above the pre-set predefined normal operating temperature, to thereby isolate the heating element from the battery 60.

A timing means, namely, a timer 65 is mounted in the hollow interior region 8 of the housing 2, and a control knob 66 of the timer 65 extends through one of the end walls 6 of the housing 2 for selectively setting a heating cycle time period during which the heating element 25 is to be operated for maintaining the temperature of the heat transfer element 30 at the predefined normal operating temperature. In this embodiment of the invention, the timer 65 can be set to time selectable predefined heating cycle time periods of twenty minutes, forty minutes and sixty minutes. The microcontroller 63 reads signals from the timer 65 for determining when the timer 65 has timed out for in turn operating the relay 72 into the open circuit state for isolating the heating element 25 from the rechargeable battery 60.

A charge control circuit 68 in the control circuit 62 monitors the charge in the rechargeable battery 60, and also controls charging of the rechargeable battery 60. A USB port 69 located in the end walls 6 beneath the control knob 66 of the timer 65 is connected to the charge control circuit 68 for receiving a low voltage DC supply from a charger unit for supply to the charge control circuit 68 for in turn charging the rechargeable battery 60.

A circular translucent ring 70 located in the end wall 6 in which the control knob 66 of the timer 65 is located extends around the control knob 66, and is illuminated by light emitting diodes 71. The light emitting diodes 71 are configured to produce two colours of light, namely, a white light and an orange light for illuminating the translucent ring 70 to glow white or orange. The light emitting diodes 71 are operated under the control of the microcontroller 63 in response to the charge control circuit 68, and are operated so that the circular translucent ring 70 glows white during normal powering of the heating element 25 by the rechargeable battery 60. During charging of the rechargeable battery 60, the light emitting diodes 71 are operating under the microcontroller 63 so that the circular translucent ring 70 glows orange. The light emitting diodes 71 are operated under the control of the microcontroller 63 to pulse orange for in turn illuminating the circular translucent ring 70 to produce a pulsed orange glow indicating that the rechargeable battery 60 requires charging.

In use, with the battery 60 charged, and with the container 15 engaged in the receiving recess 14 and with the second heat transfer abutment face 36 of the container 15 in heat conducting engagement with the first heat transfer abutment face 35 of the heat transfer disc element 29, the container 15 is charged with the appropriate amount of the desired essential oil or oils. The timer 65 is set by the control knob 66 to time the desired heating cycle time period. Setting the timer 65 to time the desired heating cycle time period automatically operates the microcontroller 63 to operate the relay 72 from the open circuit state into the closed circuit state to apply the power supply from the rechargeable battery 60 to the heating element 25. The heating element 25 quickly comes up to heat, and raises the temperature of the heat transfer element 30 and the heating element 25 to the predefined normal operating temperature, and in turn the container 15 to the predefined normal operating temperature. The microcontroller 63 continuously monitors signals from the thermistor 57 for determining the temperature of the locating element 40 and the heat transfer element 30, and controls the power supply from the battery 60 to the heating element 25 through the relay 72 for maintaining the heat transfer element 30 and the locating element 40 and in turn the container 15 at the predefined normal operating temperature. The essential oil is slowly evaporated from the container 15 through the open mouth 26 thereof at the desired evaporation rate. On the timer 65 timing out the selected heating cycle time period, the microcontroller 63 operates the relay 72 into the open circuit state, thereby isolating the heating element 25 from the power supply from the battery 60.

In the event of the temperature of the locating element 40 rising above the predefined safe operating temperature, the fuse 73 transitions into the open circuit state, thereby isolating the heating element 25 from the battery.

While the retaining means for retaining the container 15 in the receiving recess 14 has been described as comprising a permanent magnet, any other suitable magnet or retaining means may be provided. It is also envisaged that where the retaining means comprises a magnet, the magnet may be located in the container 15, and the complementary element would be located in the receiving means. Indeed, in certain cases where the container 15 is provided by a magnetic metallic material or other such magnetic material, the complementary element may be dispensed with.

While the container 15 has been described as being of a composite plastic material, the container may be of any other suitable material or desired material, and in certain cases, may be of a metal material, ceramics material, glass or other such a suitable material.

While the heating element has been described as being a planar heating element, any other suitable electrical heating elements may be provided. In certain cases, the heating element may be provided by a cartridge heater, which would be mounted in the heat transfer element.

It will also be appreciated that while the heating means has been described as being electrically powered, the heating means may be powered by any suitable source, for example, in certain cases it is envisaged that the heating means may comprise a gas powered heating means, which may be configured to convert gas to heat by flame combustion, or by catalytic conversion.

While the evaporator has been described as comprising a timer, the timer may be omitted, and in which case, an on/off switch would be provided for switching on and off the control circuit 62. Additionally, while the housing and the container have been described as being of specific shapes, the housing and the container may be of any other suitable desired shapes, however, in general, it is envisaged that the receiving recess will be of shape which would facilitate self-locating of the container in the receiving recess.

The invention claimed is:
1. An evaporator comprising:
a housing,
a container for a liquid to be evaporated,
a receiving means in the housing for releasably receiving the container supported therein,
a heating means,
a heat transfer means for transferring heat from the heating means to the container, the heat transfer means being configured to co-operate with the container for the transfer of heat from the heat transfer means to the container,
a locating means for locating and maintaining the heating means in heat conducting engagement with the heat transfer means,
a tubular element extending from the locating means in a direction away from the heating means and defining a bore extending therethrough communicating with a bore extending through the locating means, and
a retaining means located in the bore of the tubular element for releasably retaining the container in the receiving means with the container in heat conducting engagement with the heat transfer means.

2. An evaporator as claimed in claim 1 in which the heat transfer means is located in the receiving means.

3. An evaporator as claimed in claim 1 in which the heat transfer means defines a first heat transfer abutment face, and the container comprises a heat receiving portion having a second heat transfer abutment face configured to abut the first heat transfer abutment face of the heat transfer means with heat conducting.

4. An evaporator as claimed in claim 1 in which the retaining means comprises a magnet.

5. An evaporator as claimed in claim 1 in which a complementary element located in the container is provided for co-operating with the retaining means for releasably retaining the container in the receiving means.

6. An evaporator as claimed in claim 1 in which the heat transfer means defines a third heat transfer abutment face and the heating means defines a fourth heat transfer abutment face configured to abut the third heat transfer abutment face of the heat transfer means.

7. An evaporator as claimed in claim 6 in which the third and fourth heat transfer abutment faces of the heat transfer means and the heating means, respectively, are substantially planar.

8. An evaporator as claimed in claim 6 in which the heating means defines a fifth heat transfer abutment face opposite the fourth heat transfer abutment face thereof engageable with a sixth heat transfer abutment face defined by the locating means with heat conducting engagement.

9. An evaporator as claimed in claim 8 in which the sixth heat transfer abutment face of the locating means is coated with an electrically insulating coating.

10. An evaporator as claimed in claim 6 in which the third heat transfer abutment face of the heat transfer means is coated with an electrically insulating coating.

11. An evaporator as claimed in claim 1 in which an engagement means extending from the heat transfer means is engageable with an opening in the receiving means for securing the heat transfer means in the receiving means.

12. An evaporator as claimed in claim 11 in which the locating means is located within the engagement means of the heat transfer means and is retained in abutting engagement with the heating means by the engagement means with the heating means retained tightly sandwiched between the locating means and the heat transfer means.

13. An evaporator as claimed in claim 1 in which the housing defines a hollow interior region, the receiving means comprising a receiving recess formed in the housing, and a partition element of the housing separates the receiving recess from the hollow interior region of the housing, and the engagement means of the heat transfer means is configured for engaging an opening in the partition element.

14. An evaporator as claimed in claim 1 in which the heating means is configured to be electrically powered, and comprises a planar heating element.

15. An evaporator as claimed in claim 14 in which the planar heating element of the heating means comprises an elongated heating element configured in a serpentine shape.

16. An evaporator as claimed in claim 1 in which the locating means is configured to transfer heat from the heating means to the retaining means, and the retaining means extends through an opening defined by the heating means and into a bore in the heat transfer means for transferring heat from the locating means to the heat transfer means.

17. An evaporator as claimed in claim 1 in which a temperature sensing means is provided for monitoring the temperature of the heat transfer means.

18. An evaporator as claimed in claim 17 in which a control means is provided for controlling the heating means in response to temperature sensed by the temperature sensing means for maintaining the temperature of the heat transfer means at a predefined normal operating temperature.

19. An evaporator as claimed in claim 17 in which the temperature sensing means is located in the bore extending through the tubular element of the locating means.

20. An evaporator as claimed in claim 1 in which the heat transfer means comprises a planar element.

* * * * *